(12) United States Patent
Ono

(10) Patent No.: US 12,029,827 B2
(45) Date of Patent: Jul. 9, 2024

(54) STERILIZING APPARATUS

(71) Applicant: SHINKO SANGYO CO. LTD., Kobe (JP)

(72) Inventor: Mototsugu Ono, Kobe (JP)

(73) Assignee: Shinko Sangyo Co. Ltd., Kobe (JP)

( * ) Notice: Subject to any disclaimer, the term of this patent is extended or adjusted under 35 U.S.C. 154(b) by 589 days.

(21) Appl. No.: 17/328,067

(22) Filed: May 24, 2021

(65) Prior Publication Data

US 2022/0008587 A1  Jan. 13, 2022

(30) Foreign Application Priority Data

Jul. 13, 2020 (JP) ................ 2020-120180

(51) Int. Cl.
*A61L 2/22* (2006.01)
*A61L 2/24* (2006.01)
*A61L 2/26* (2006.01)

(52) U.S. Cl.
CPC ............ *A61L 2/22* (2013.01); *A61L 2/24* (2013.01); *A61L 2/26* (2013.01); *A61L 2202/15* (2013.01); *A61L 2202/16* (2013.01); *A61L 2202/25* (2013.01)

(58) Field of Classification Search
CPC ..... A61L 2/22; A61L 2/24; A61L 2/26; A61L 2202/15; A61L 2202/16; A61L 2202/25
See application file for complete search history.

(56) References Cited

U.S. PATENT DOCUMENTS

| | | | |
|---|---|---|---|
| 3,826,612 A * | 7/1974 | Black | .......... A61L 2/07 422/112 |
| 5,713,519 A | 2/1998 | Sandison et al. | |
| 2004/0050877 A1 | 3/2004 | Ono | |
| 2015/0136184 A1 | 5/2015 | Kim | |
| 2019/0060938 A1* | 2/2019 | Whiting | .......... B05B 13/0421 |

FOREIGN PATENT DOCUMENTS

| | | | |
|---|---|---|---|
| CN | 107185006 A * | 9/2017 | ........... A61L 2/18 |
| JP | S6155952 U | 4/1986 | |
| JP | 62-57696 U | 4/1987 | |
| JP | H0253148 U | 4/1990 | |
| JP | H11509472 A | 8/1999 | |

(Continued)

OTHER PUBLICATIONS

Machine Translation of CN 107185006 (Year: 2017).*

(Continued)

*Primary Examiner* — Lessanework Seifu
(74) *Attorney, Agent, or Firm* — Ruggiero McAllister & McMahon LLC

(57) ABSTRACT

An example sterilizing apparatus comprises a medical fluid container storing a medical fluid containing alcohol, a gas cylinder filled with pressurized carbon dioxide gas, and a spray gun connected with the medical fluid container and the gas cylinder. The sterilizing apparatus being configured to spray the medical fluid into a target space under action of the carbon dioxide gas injected from a tip nozzle of the spray gun. The sterilizing apparatus further comprises a control valve to increase and/or decrease an amount of the carbon dioxide gas to be injected, thus adjusting an amount of the medical fluid to be sprayed.

5 Claims, 7 Drawing Sheets

(56) References Cited

FOREIGN PATENT DOCUMENTS

| | | |
|---|---|---|
| JP | 3066673 U | 12/1999 |
| JP | 3754407 B2 | 3/2006 |
| KR | 200489931 Y1 * | 8/2019 |

OTHER PUBLICATIONS

Machine Translation of KR 200489931 (Year: 2019).*
Japanese Decision of Refusal dated Jun. 30, 2022 and mailed Jul. 5, 2022 from corresponding Japanese Patent Application No. 2020-120180, p. 1-5.
Japanese Office Action dated Apr. 26, 2022 from corresponding Japanese Patent Application No. 2020-120180, 4 pages.

* cited by examiner

STERILIZING APPARATUS

CROSS-REFERENCE TO RELATED APPLICATIONS

This non-provisional application claims priority under 35 U.S.C. § 119 to Japanese Patent Application No. 2020-120180 filed in Japan on Jul. 13, 2020, the entire contents of which are hereby incorporated by reference.

FIELD

The present disclosure relates to sterilizing apparatuses.

BACKGROUND AND SUMMARY

There has been a sterilizing apparatus to convert a medical fluid composed mainly of alcohol into particulates and spray the particulate medical fluid into a target space so as to sterilize the target space.

For example, the apparatus includes a spray gun such as those used widely for coating. A medical fluid tank storing the above-mentioned medical fluid is attached to the spray gun. A gas cylinder storing carbon dioxide gas serving as a carrier gas is connected to the spray gun. The carbon dioxide gas is injected from a tip nozzle of the spray gun. Under the action of negative pressure generated during this injection, the medical fluid within the medical fluid tank is sucked up, converted into particulates, and sprayed.

The medical fluid in the form of particles to be sprayed is composed mainly of high concentration alcohol and thus has the risk of catching fire and causing an explosion. The medical fluid, however, is scattered uniformly while being surrounded by the carbon dioxide gas and protected from oxygen within the target space. An operator is thus able to carry out a sterilizing operation without regard for presence or absence of fire. Alcohol dries quickly and does not remain for a long time after adhering to, for example, a wall surface or a floor surface in the target space.

This saves time and effort required for a post-sterilizing process including wiping. Accordingly, the operator is able to carry out the sterilizing operation for the target space highly efficiently and successfully.

Sterilizing operations such as that described above are carried out on various target spaces. When clean rooms of pharmaceutical companies or patients' rooms in hospitals, for example, are targeted for such sterilizing operations, reliable sterilizing processes need to be performed by scattering large amounts of medical fluids. When interiors of ambulances or kitchens of grocery stores, for example, are targeted for such sterilizing operations, sterilizing processes, including post-sterilizing processes, need to be finished in a short time. Unfortunately, the sterilizing apparatus is not intended to meet different needs for different target spaces.

The sterilizing apparatus is brought into a target space, and the spray gun is held in an operator's hand when the medical fluid is sprayed therefrom. The operator, however, needs to wear protectors, such as a mask and goggles, which increases the burden on the operator.

An object of the present disclosure is to provide a sterilizing apparatus that is able to meet different needs for different target spaces and is successfully adaptable to various target spaces.

According to an aspect of disclosure, there is provided a sterilizing apparatus comprising: a medical fluid container storing a medical fluid containing alcohol; a gas cylinder filled with pressurized carbon dioxide gas; and a spray gun connected with the medical fluid container and the gas cylinder, the sterilizing apparatus being configured to spray the medical fluid into a target space under action of the carbon dioxide gas injected from a tip nozzle of the spray gun, wherein the sterilizing apparatus further comprises a control valve to increase and/or decrease an amount of the carbon dioxide gas to be injected, thus adjusting an amount of the medical fluid to be sprayed.

According to another aspect of disclosure, the sterilizing apparatus further comprises a gas hose extending from the gas cylinder and connected to the spray gun, wherein the control valve is interposed between the gas hose and the spray gun.

According to another aspect of disclosure, the medical fluid container is connected to the spray gun through a flexible medical fluid hose.

According to another aspect of disclosure, the sterilizing apparatus further comprises a mounting stand to which the spray gun is attached, the mounting stand being configured to rotate the spray gun around an axis extending in an up-down direction above a floor surface in the target space.

According to another aspect of disclosure, the sterilizing apparatus further comprises a reverse selector to automatically reverse a rotation direction of the spray gun for each predetermined angle.

According to another aspect of disclosure, the spray gun is attached to the mounting stand such that the spray gun is changeable in elevation angle.

According to another aspect of disclosure, the sterilizing apparatus further comprises a timer setter and a solenoid selector valve that opens and closes in accordance with setting of the timer setter so as to allow selection between supply and interruption of the carbon dioxide gas to the spray gun.

The present disclosure may meet different needs for different target spaces and sterilize various target spaces under suitable conditions.

The above and further objects and features will more fully be apparent from the following detailed description with accompanying drawings.

DETAILED DESCRIPTION OF NON-LIMITING EXAMPLE EMBODIMENTS

Embodiments of the present disclosure will be described below with reference to the drawings.

Embodiment 1

Figure 1:
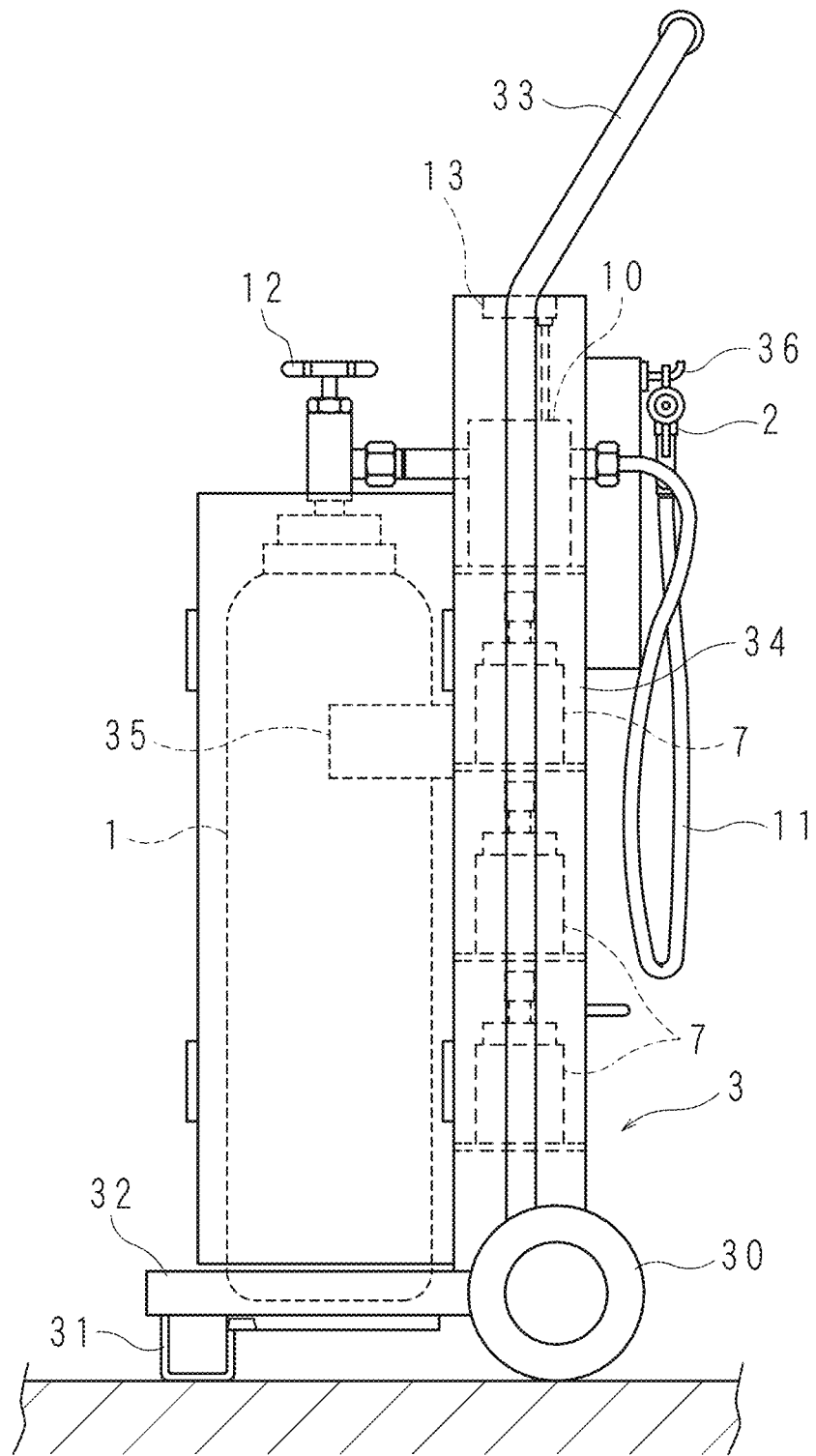
FIG. 1 is a side view of a sterilizing apparatus according to Embodiment 1.
Figure 2:
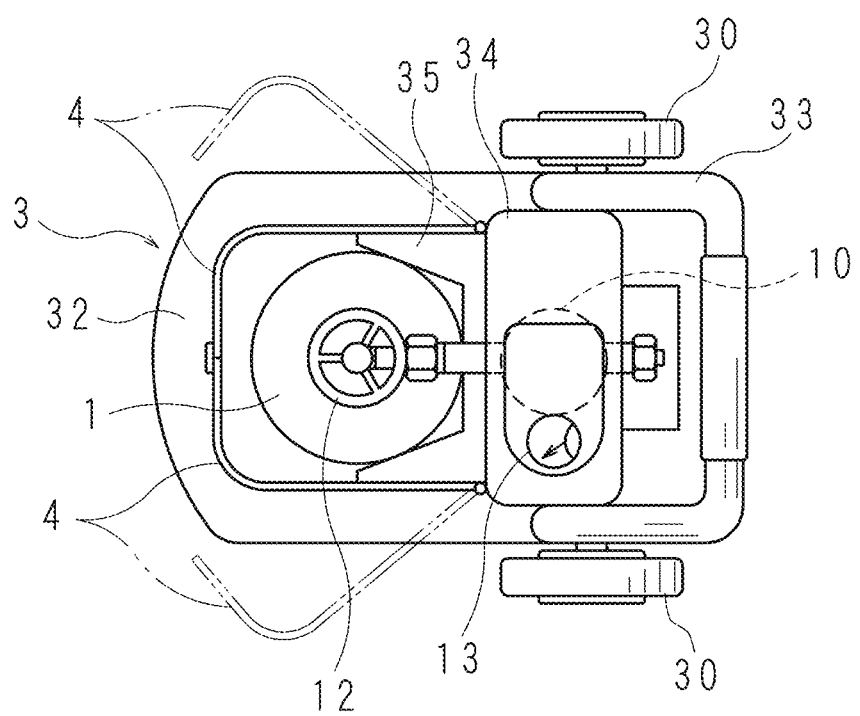
FIG. 2 is a plan view of the sterilizing apparatus according to Embodiment 1 as viewed from above.

FIG. 1 is a side view of a sterilizing apparatus according to Embodiment 1. FIG. 2 is a plan view of the sterilizing apparatus as viewed from above.

As illustrated in FIGS. 1 and 2, the sterilizing apparatus according to Embodiment 1 includes: a gas cylinder 1 filled with pressurized carbon dioxide gas serving as a carrier gas; and a spray gun 2 connected to a discharge port of the gas cylinder 1 through a pressure reducing valve 10 and a gas hose 11.

The gas cylinder 1 is installed on a cart 3. The cart 3 includes a base 32 supported by a pair of wheels 30, 30 and a supporting leg 31 such that the base 32 is substantially parallel to a floor surface. The base 32 is provided with a gripping pipe 33 extending vertically upward from locations on the wheels 30, 30. A holding box 34 is provided between legs of the gripping pipe 33.

The gas cylinder 1 is placed on a central region of the upper surface of the base 32, with the discharge port facing upward. An intermediate portion of the gas cylinder 1 in its height direction is supported by a support 35 protruding from the holding box 34, so that the gas cylinder 1 in an upright position is fixed onto the base 32 as illustrated in FIG. 1. As illustrated in FIG. 2, the support 35 includes a recess that is in contact with and supports the peripheral surface of a body of the gas cylinder 1 at three points. The gas cylinder 1 is thus fixed while its stable position is maintained. A belt (not illustrated) may be provided between the ends of the support 35, and the gas cylinder 1 may be fixed more securely by tightening the belt around the gas cylinder 1.

The outer portion of the gas cylinder 1 fixed in this manner is covered with a box-shaped exterior cover 4 in order to protect the gas cylinder 1 from collision of objects. The exterior cover 4 is openable and closable. The gas cylinder 1 is attachable to and detachable from the cart 3 when the exterior cover 4 is opened as indicated by the chain double-dashed lines in FIG. 2.

The discharge port of the gas cylinder 1 protrudes above the exterior cover 4 and faces a first surface of the holding box 34. The discharge port of the gas cylinder 1 is openable and closable by an on-off valve 12. The carbon dioxide gas pressurized and filled into the gas cylinder 1 is discharged from the discharge port and supplied to the spray gun 2 through the pressure reducing valve 10 and the gas hose 11 by opening the on-off valve 12.

As indicated by the broken line in FIG. 1, the pressure reducing valve 10 is housed and held in the upper portion of the holding box 34. The entry side of the pressure reducing valve 10 is protruded from the first surface of the holding box 34 and connected to the discharge port of the gas cylinder 1. The exit side of the pressure reducing valve 10 is protruded from a second surface of the holding box 34 and connected to a first end of the flexible gas hose 11. The spray gun 2 (which will be described below) is connected to a second end of the gas hose 11. The upper portion of the second surface of the holding box 34 is provided with a gun hook 36. As illustrated in FIG. 1, the spray gun 2 in a non-use state is hooked on the gun hook 36 for storage. In FIG. 2, neither the gas hose 11 nor the spray gun 2 is illustrated.

The pressure reducing valve 10 is a known valve having the function of reducing the pressure of high pressure gas, which is delivered from the entry side, to a predetermined pressure and delivering the resulting gas to the exit side. The pressure reducing valve 10 is set to reduce the pressure of carbon dioxide gas within the gas cylinder 1 to a constant pressure of about 0.2 MPa to about 0.5 MPa and deliver the resulting carbon dioxide gas to the spray gun 2 through the gas hose 11 connected to the exit side. As illustrated in FIG. 2, a pressure gauge 13 to detect the pressure at the exist side of the pressure reducing valve 10 is fitted to the upper surface of the holding box 34 such that the pressure gauge 13 is visible from above.

Figure 3:
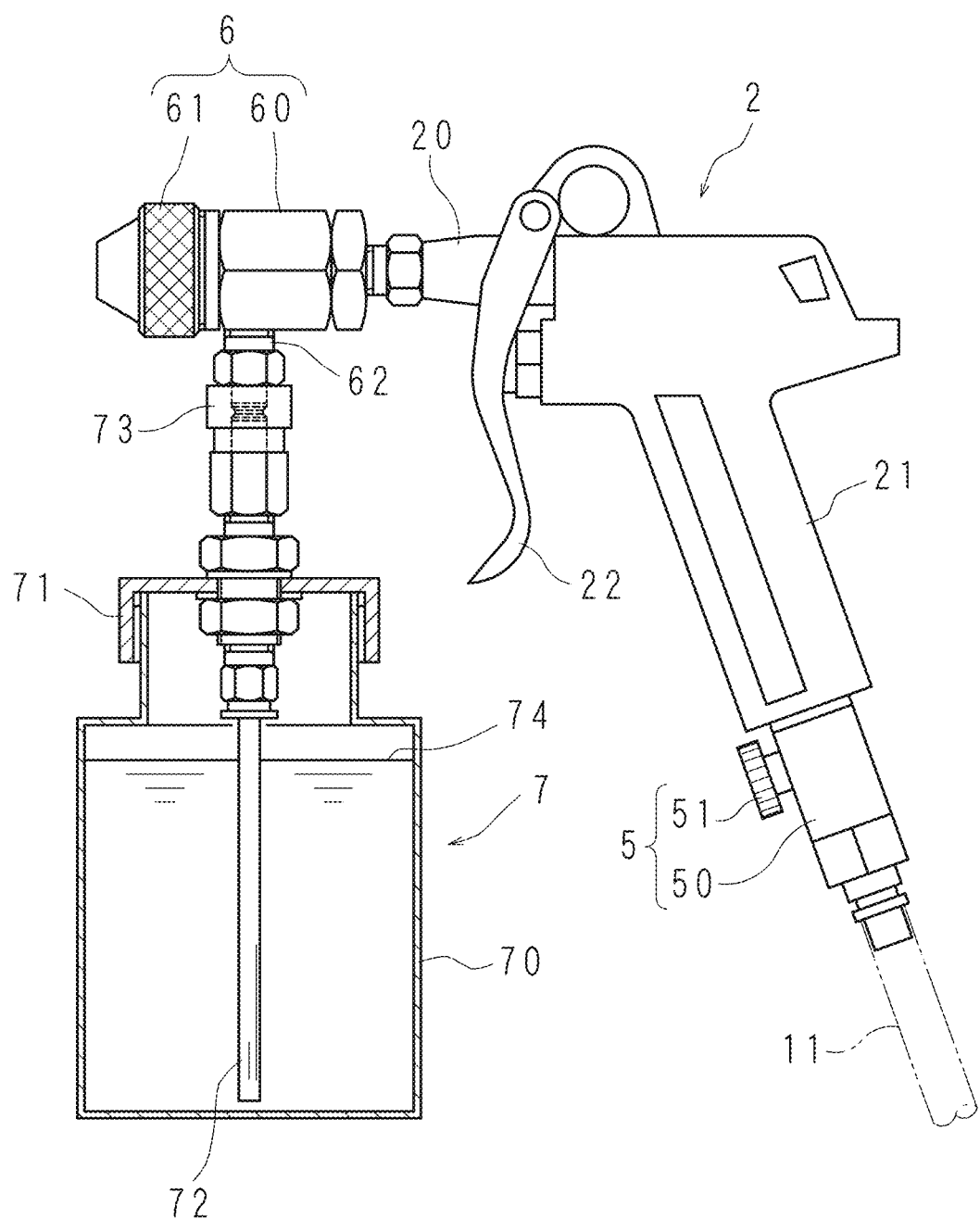
FIG. 3 is a side view of a spray gun, illustrating its structure.

FIG. 3 is a side view of the spray gun 2, illustrating its structure. The spray gun 2 includes a barrel 20, a grip 21, and a trigger 22. The gas hose 11 is connected to a base end of the grip 21. A control valve 5 is disposed on the connection between the gas hose 11 and the base end of the grip 21 such that the control valve 5 is interposed therebetween. The tip of the barrel 20 is fitted with a tip nozzle 6. A gas passage (not illustrated) is defined inside the barrel 20 and the grip 21. The carbon dioxide gas delivered from the gas hose 11 flows into the gas passage through the control valve 5. The carbon dioxide gas is supplied to the tip nozzle 6 on the tip of the barrel 20 by pulling the trigger 22.

The control valve 5 includes: a tubular valve body 50 continuous with the base end of the grip 21; and an adjusting dial 51 provided on the peripheral surface of the valve body 50. The adjusting dial 51 is rotatable while being held from outside the valve body 50. Rotating the adjusting dial 51 enables a valve element inside the valve body 50 to change its orientation so as to increase and/or decrease the degree of opening of the control valve 5, thus adjusting the amount of carbon dioxide gas to be supplied to the tip nozzle 6 through the gas passage.

Figure 4A:
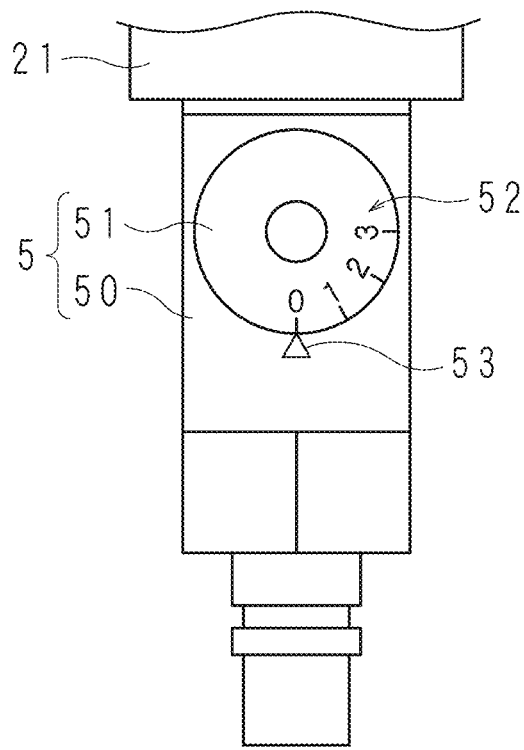
FIGS. 4A and 4B are plan views of an example of an adjusting dial.
Figure 4B:
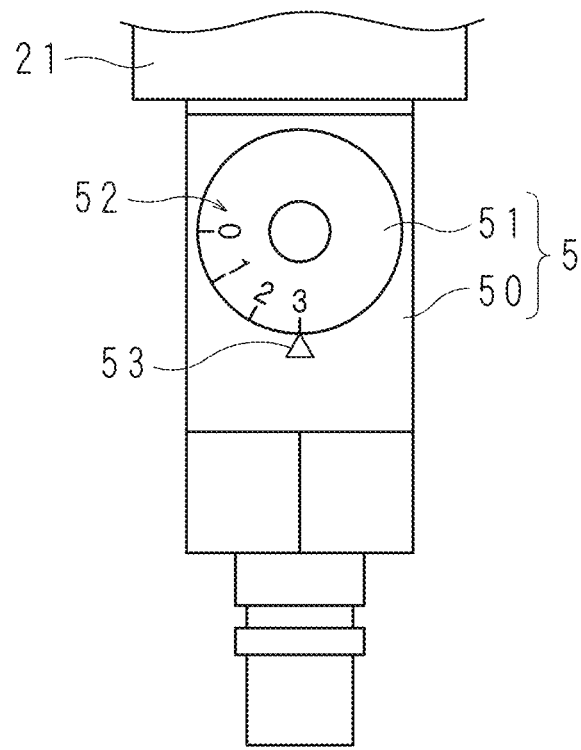

FIGS. 4A and 4B are plan views of an example of the adjusting dial 51. The adjusting dial 51 illustrated in FIGS. 4A and 4B has a disk shape. The adjusting dial 51 is rotatable around an axis perpendicular to the valve body 50. The surface of the adjusting dial 51 is provided with a graduation line 52 marked with numbers "0", "1", "2", and "3" each indicative of the degree of opening. The outer periphery of the valve body 50 is provided with an eye mark 53 having a triangular arrow shape. The degree of opening of the control valve 5 is determinable from outside by reading the number on the graduation line 52 brought into alignment with the eye mark 53.

FIG. 4A illustrates the adjusting dial 51, with the number "0" on the graduation line 52 brought into alignment with the eye mark 53. In this state, the control valve 5 is closed such that supply of carbon dioxide gas to the tip nozzle 6 is cut off. FIG. 4B illustrates the adjusting dial 51, with the number "3" on the graduation line 52 brought into alignment with the eye mark 53. In this state, the control valve 5 is fully opened such that the amount of carbon dioxide gas to be supplied to the tip nozzle 6 is, for example, 75 L/min at the maximum. The amount of carbon dioxide gas to be supplied decreases sequentially by bringing the numbers "2" and "1" on the graduation line 52 into alignment with the eye mark 53. For example, the amount of carbon dioxide gas to be supplied will be 60 L/min by bringing the number "2" into alignment with the eye mark 53 and will be 40 L/min by bringing the number "1" into alignment with the eye mark 53.

The adjusting dial 51 may be rotatable continuously or gradually between the numbers "0" and "3" on the graduation line 52. An adjustment to the degree of opening of the control valve 5 does not necessarily have to be made by rotating the adjusting dial 51 but may alternatively be made by any other operations, such as a button operation or a lever operation.

The tip nozzle 6 includes a tubular nozzle body 60 and a nozzle head 61 fixed to an extremity of the nozzle body 60. The peripheral surface of the nozzle body 60 is connected with a communication pipe 62 extending in a direction substantially perpendicular to the peripheral surface of the nozzle body 60. An extremity of the communication pipe 62 is fitted with a medical fluid container 7.

As illustrated in cross section in FIG. 3, the medical fluid container 7 includes: a bottle-shaped container body 70; a lid plate 71 screwed to the peripheral edge of the container body 70 such that an opening of the container body 70 is sealed; and a suction pipe 72 passing through the center of the lid plate 71 and extending to the vicinity of the bottom surface of the container body 70. The outer end of the suction pipe 72 is connected to an end of the communication pipe 62 through a coupler 73 so as to be detachably attached to the tip nozzle 6.

A medical fluid 74 for sterilization is stored in the container body 70. The medical fluid 74 is prepared, for example, by mixing a water-soluble sterilizing agent into a liquid medicine composed mainly of alcohol. The medical fluid 74 has a composition adjusted such that the concentration of alcohol is 65 percent to 80 percent by volume. The sterilizing agent to be mixed may be suitably selected in accordance with the type(s) of germ(s) regarded as target(s) for sterilization. More than one medical fluid container 7 may be prepared such that different types of medical fluids 74 are stored in the medical fluid containers 7. As illustrated in FIG. 1, the medical fluid containers 7 may be stored in a storage space provided in the holding box 34 on the cart 3. When in use, the medical fluid container(s) 7 may be suitably replaced in accordance with target location(s) or the type(s) of germ(s).

Figure 5:
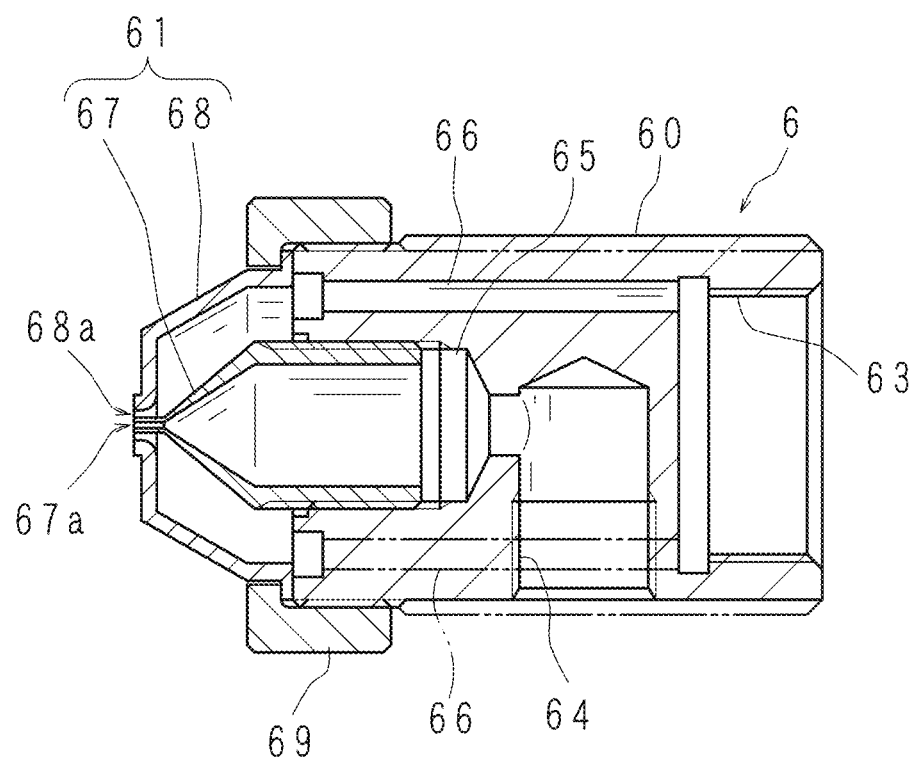
FIG. 5 is a longitudinal cross-sectional view of a tip nozzle.

FIG. 5 is a longitudinal cross-sectional view of the tip nozzle 6. As illustrated in FIG. 5, a base end of the nozzle body 60 is provided with a coupling hole 63 for coupling with the spray gun 2. The outer peripheral surface of an intermediate portion of the nozzle body 60 is provided with a connecting hole 64 for connection with the communication pipe 62. The connecting hole 64 is in communication with the extremity of the nozzle body 60 through a medical fluid passage 65 defined in an axial center portion of the nozzle body 60. The coupling hole 63 is in communication with the extremity of the nozzle body 60 through a plurality of gas passages 66 defined equidistantly outward of the medical fluid passage 65.

The nozzle head 61 includes: an inner nozzle 67 screwed into an end of the medical fluid passage 65 so as to be fixed thereto; and an outer nozzle 68 surrounding the outer portion of the inner nozzle 67. The outer nozzle 68 is provided on its peripheral edge with a flange. The flange is clamped between an end face of the nozzle body 60 and a stopper ring 69 such that the outer nozzle 68 is fixed to the nozzle body 60. The inner nozzle 67 and the outer nozzle 68 are each in the form of a funnel shape tapered toward its tip. The tip of the inner nozzle 67 is provided with a small-diameter fluid injection port 67a. The tip of the outer nozzle 68 is provided with an annular gas injection port 68a defined between the tip of the outer nozzle 68 and the fluid injection port 67a. The medical fluid passage 65 is in communication with the inside of the inner nozzle 67. The gas passages 66 are in communication with an annular space defined between the outer nozzle 68 and the inner nozzle 67.

The sterilizing apparatus according to Embodiment 1, which is structured as described above, is used in the following manner. The on-off valve 12 on the upper end of the gas cylinder 1 is opened, the grip 21 of the spray gun 2 is held such that the tip of the tip nozzle 6 is directed to the inside of a target space, and then the trigger 22 is pulled. Thus, the pressure of carbon dioxide gas within the gas cylinder 1 is reduced to a predetermined pressure by the pressure reducing valve 10, and the carbon dioxide gas subsequently flows through the gas hose 11, the control valve 5, and the spray gun 2 so as to reach the tip nozzle 6. The carbon dioxide gas is introduced into the outer nozzle 68 of the nozzle head 61 through the gas passages 66 defined in the nozzle body 60 and is then injected to the outside from the gas injection port 68a provided in the tip of the outer nozzle 68.

Injecting the carbon dioxide gas in this manner generates negative pressure around the fluid injection port 67a in the tip of the inner nozzle 67, so that the inside of the inner nozzle 67 and the inside of the medical fluid passage 65, the connecting hole 64, and the communication pipe 62 are placed under negative pressure. As a result, the medical fluid 74 within the medical fluid container 7 connected to the communication pipe 62 is sucked up into the suction pipe 72, flows through the connecting hole 64 and the medical fluid passage 65 so as to reach the fluid injection port 67a opened in the tip of the inner nozzle 67, and is then sprayed in the form of minute diameter particles.

The particle diameter of the medical fluid 74 to be sprayed is set to be 15 μm to 20 μm by properly designing the nozzle head 61 (or in particular, the gas injection port 68a and the fluid injection port 67a). The medical fluid 74 sprayed in the form of particles having such a particle diameter spreads widely throughout the target space, drifts while slowly settling down, and then adheres to surfaces in the target space, such as a floor surface and a wall surface. In the course of this process, the target space is sterilized by the action of alcohol, which is the main component of the medical fluid 74, and the sterilizing agent added thereto.

The medical fluid 74 is sprayed while being surrounded by the carbon dioxide gas, and the particles of alcohol, which is the main component of the medical fluid 74, are thus protected from oxygen within the target space. This makes it possible to achieve a high sterilizing effect while avoiding the risk of catching fire immediately after spraying. Because the medical fluid 74 sprayed is composed mainly of alcohol that dries quickly, the medical fluid 74 vaporizes rapidly without remaining for a long time after adhering to regions in the target space. Accordingly, there will be no possibility of multiplication of new various germs induced by residual moisture, making it possible to save the time and effort of post-sterilizing process including wiping.

The amount of the medical fluid 74 to be sprayed is responsive to the injection amount of carbon dioxide gas serving as a carrier gas. The sterilizing apparatus according to the present disclosure includes the control valve 5. Operating the control valve 5 as described above enables an increase and/or a decrease in the amount of carbon dioxide gas to be supplied to the tip nozzle 6, i.e., the amount of carbon dioxide gas to be injected from the tip nozzle 6, thus making it possible to change the amount of the medical fluid 74 to be sprayed.

As previously mentioned, the injection amount of carbon dioxide gas may be 75 L/min, 60 L/min, or 40 L/min. When the injection amount of carbon dioxide gas is 75 L/min, the amount of the medical fluid 74 to be sprayed will be 120 mL/min. When the injection amount of carbon dioxide gas is 60 L/min, the amount of the medical fluid 74 to be sprayed will be 100 mL/min. When the injection amount of carbon dioxide gas is 40 L/min, the amount of the medical fluid 74 to be sprayed will be 60 mL/min. The amount of the medical fluid 74 to be sprayed is thus changeable and adaptable to the needs of the target space. For the target space that requires a reliable sterilizing process, for example, the amount of the medical fluid 74 to be sprayed is preferably increased. For the target space that requires a sterilizing process to be finished in a short time, the amount of the medical fluid 74 to be sprayed is preferably decreased so as to reduce the time necessary for the sterilizing process including a post-sterilizing process.

The amount of the medical fluid 74 to be sprayed is easily adjustable by operating the adjusting dial 51 of the control valve 5. The control valve 5 is provided on the connection between the grip 21 of the spray gun 2 and the gas hose 11. The amount of the medical fluid 74 to be sprayed is suitably adjustable by operating the adjusting dial 51 during sterilizing operation.

The sterilizing process carried out as described above may cause continuously injected carbon dioxide gas to freeze in the vicinity of the discharge port of the gas cylinder 1 owing to cubical expansion incident to pressure reduction through the pressure reducing valve 10. The timing of such freezing may be delayed by properly setting the amount of carbon dioxide gas to be delivered. The time required for necessary continuous injection of carbon dioxide gas is about a few or several minutes except when the target space is excessively large. It is verified that carbon dioxide gas is continuously injectable for about a few or several minutes without being frozen, and carbon dioxide gas is continuously injectable for 15 minutes or longer by optimally designing the gas hose 11, the spray gun 2, and the tip nozzle 6.

The possibility of freezing mentioned above is reduced by opening the exterior cover 4, which covers the outer portion of the gas cylinder 1, and conducting heat exchange between the peripheral wall of the gas cylinder 1 and outside air. In particular, when a sterilizing operation is performed for a long time under conditions where the amount of carbon dioxide gas to be injected is large, the exterior cover 4 is preferably opened as indicated by the chain double-dashed lines in FIG. 2.

The gas cylinder 1 filled with pressurized carbon dioxide gas is commercially available. Commercially available gas cylinders, which are usable as the gas cylinder 1, include those with various internal capacities, such as 1 Kg, 3 Kg, and 5 Kg. Accordingly, a gas cylinder with a suitable internal capacity may be selected and used as the gas cylinder 1. If a large-size gas cylinder with an internal capacity of 5 Kg, for example, is used as the gas cylinder 1, the weight of the sterilizing apparatus, including the pressure reducing valve 10, the gas hose 11, the spray gun 2, and the tip nozzle 6, would be about 20 Kg. Thus, the components of the sterilizing apparatus are collectively installable on the cart 3 having a simple structure illustrated in FIG. 1, and the cart 3 is inclinable by holding the gripping pipe 33, so that the cart 3 is freely movable by rolling of the wheels 30, 30. Consequently, sterilizing processes for patients' rooms in hospitals and interiors of ambulances, for example, are carried out speedily and easily.

Variation

In Embodiment 1 described above, the medical fluid container 7 is attached to the spray gun 2. Alternatively, a large-capacity medical fluid container 7 may be used. In such a variation, an operator may convey the medical fluid container 7 by carrying it on his or her back, or may install the medical fluid container 7 on the cart 3 and convey the medical fluid container 7 together with the gas cylinder 1. The medical fluid container 7 may be connected to the spray gun 2 through a flexible medical fluid hose with a suitable length such that the medical fluid is injected as described above. This variation enables the operator to hold the spray gun 2 light in weight in his or her hand, making it possible to save labor and reduce the burden on the operator.

Embodiment 2

Figure 6:
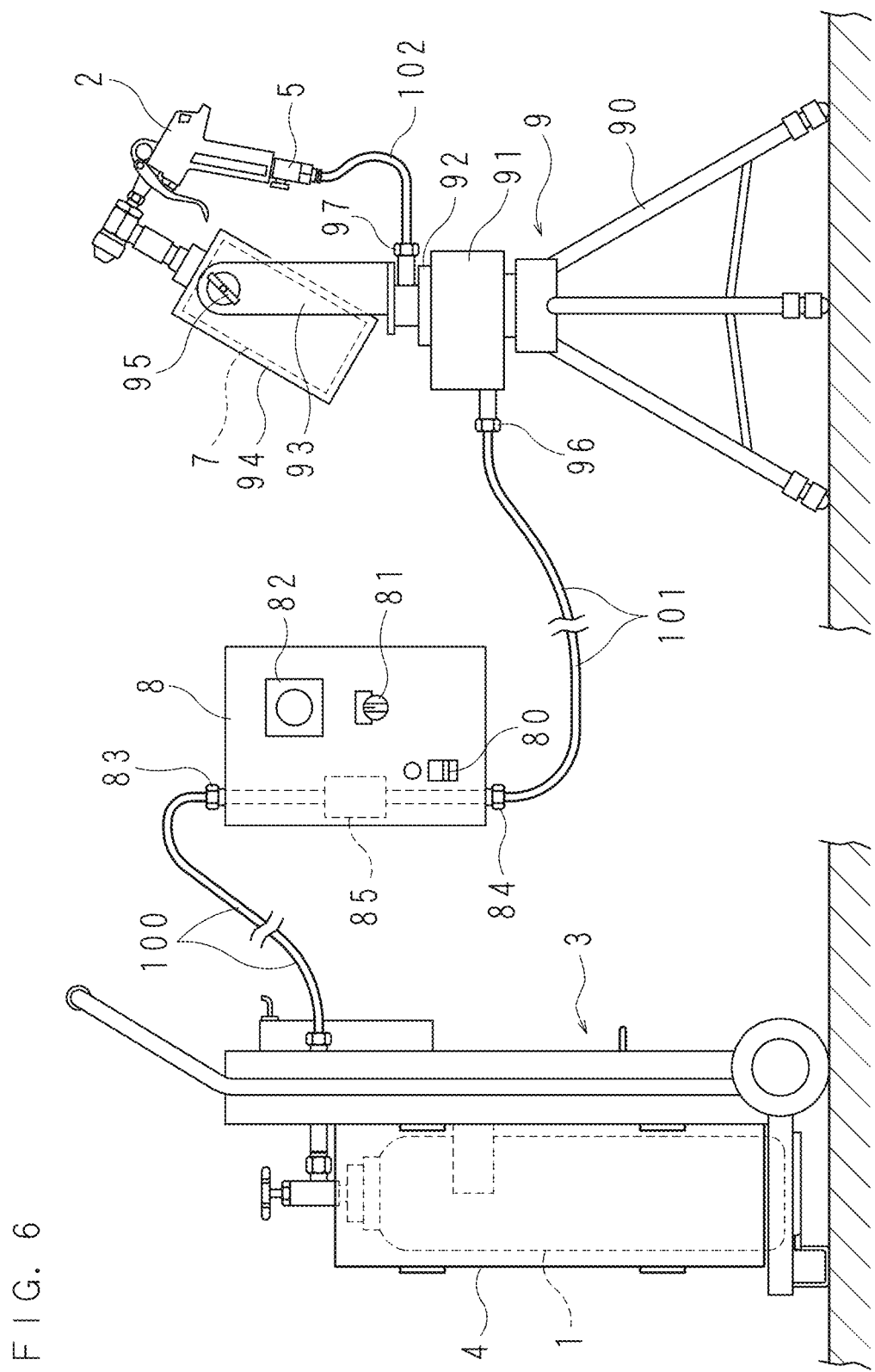
FIG. 6 is a schematic diagram illustrating an overall structure of a sterilizing apparatus according to Embodiment 2.

A sterilizing apparatus according to Embodiment 2 is structured to be able to sterilize the inside of a target space in an unlimited manner. FIG. 6 is a schematic diagram illustrating an overall structure of the sterilizing apparatus according to Embodiment 2. Similarly to Embodiment 1, the sterilizing apparatus illustrated in FIG. 6 includes: a gas cylinder 1 filled with pressurized carbon dioxide gas; and a spray gun 2 to spray a medical fluid using, as a carrier gas, the carbon dioxide gas supplied from the gas cylinder 1. The sterilizing apparatus according to Embodiment 2 further includes: a control panel 8 for operating the sterilizing apparatus; and a mounting stand 9 for the spray gun 2.

Similarly to Embodiment 1, the gas cylinder 1 having its periphery surrounded by an exterior cover 4 is installed on a cart 3 and is suitably movable together with the cart 3. A discharge port on the upper end of the gas cylinder 1 is connected with a first end of an output hose 100 through a pressure reducing valve (not illustrated). The carbon dioxide gas within the gas cylinder 1 is delivered to the output hose 100 after having been reduced in pressure through the pressure reducing valve. The cart 3 is similar in structure to that described in Embodiment 1 and will thus not be described in detail.

The control panel 8 includes a control surface on which a power switch 80, an operation selector switch 81, and a timer setter 82 are provided. The control panel 8 is placed on, for example, a wall surface in a room or a dedicated base, with the control surface facing the front, and is connected to a commercial power supply when in use. The power switch 80 is a switch to connect the components of the control panel 8 to the commercial power supply. The operation selector switch 81 is a switch to select a mode of operation from among a manual operation, an automatic operation, and a non-operation mode. The timer setter 82 is provided to set, for example, the start time, operation time, and end time of the automatic operation.

The control panel 8 is provided with an entry side connection 83 and an exit side connection 84 respectively protruded from the upper and lower surfaces of the control panel 8. The entry side connection 83 is connected with a second end of the output hose 100 mentioned above. The exit side connection 84 is connected with a first end of a first coupling hose 101. The entry side connection 83 and the exit side connection 84 are connected to a solenoid selector valve 85 provided inside the control panel 8. Upon opening of the solenoid selector valve 85, the carbon dioxide gas within the output hose 100 is delivered to the first coupling hose 101.

When the automatic operation is selected by operating the operation selector switch 81, the solenoid selector valve 85 is opened at the start time and is then closed after a lapse of the operation time. The solenoid selector valve 85 is opened when the manual operation is selected and is closed when the non-operation mode is selected.

The mounting stand 9 includes a driving box 91 supported above a floor surface such that the height of the driving box 91 is adjustable by a tripod 90. The upper surface of the driving box 91 is provided with a rotating table 92. The rotating table 92 is driven by a motor (not illustrated) incorporated into the driving box 91 and is thus rotated around an axis extending in an up-down direction. The rotating table 92 is provided with a supporting leg 93 extending vertically therefrom. The supporting leg 93 supports a holder 94. The holder 94 is pivotally supported by the upper end of the supporting leg 93 such that the holder 94 is swingable around its horizontal axis. The holder 94 is fixable at a suitable inclination angle by tightening a lock nut 95 on a pivotally supported portion of the holder 94.

A lateral surface of the driving box 91 is provided with an entry side connection 96 protruding therefrom. A lateral surface of the rotating table 92 is provided with an exit side connection 97 protruding therefrom. The entry side connection 96 is connected with a second end of the first coupling hose 101 mentioned above. The exit side connection 97 is connected with a first end of a second coupling hose 102. The entry side connection 96 and the exit side connection 97 are in communication with each other through a gas passage passing through the rotation axis of the rotating table 92 inside the driving box 91. The carbon dioxide gas within the first coupling hose 101 is thus delivered to the second coupling hose 102.

A medical fluid container 7 attached to the spray gun 2 as illustrated in FIG. 3 is held by the holder 94. The spray gun 2 is thus attached to the mounting stand 9 using the medical fluid container 7 as a support. The spray gun 2 attached to the mounting stand 9 in this manner is connected to a second end of the second coupling hose 102. As previously described, the spray gun 2 sprays the medical fluid within the medical fluid container 7 using, as a carrier gas, the carbon dioxide gas delivered from the second coupling hose 102.

The holder 94 holding the spray gun 2 is fixable at a suitable inclination angle as mentioned above. The elevation angle of the spray gun 2 is changeable by changing the inclination angle of the holder 94. The holder 94 is supported by the supporting leg 93 extending vertically from the rotating table 92. The spray gun 2 sprays the medical fluid at a suitable elevation angle while rotating together with the rotating table 92.

Figure 7A:
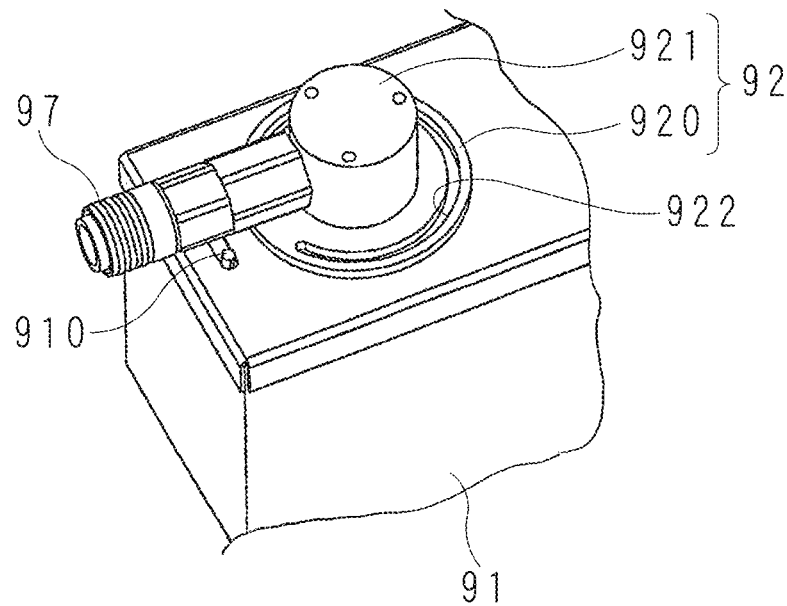
FIGS. 7A and 7B are upper perspective views of a rotating table, illustrating its structure.
Figure 7B:
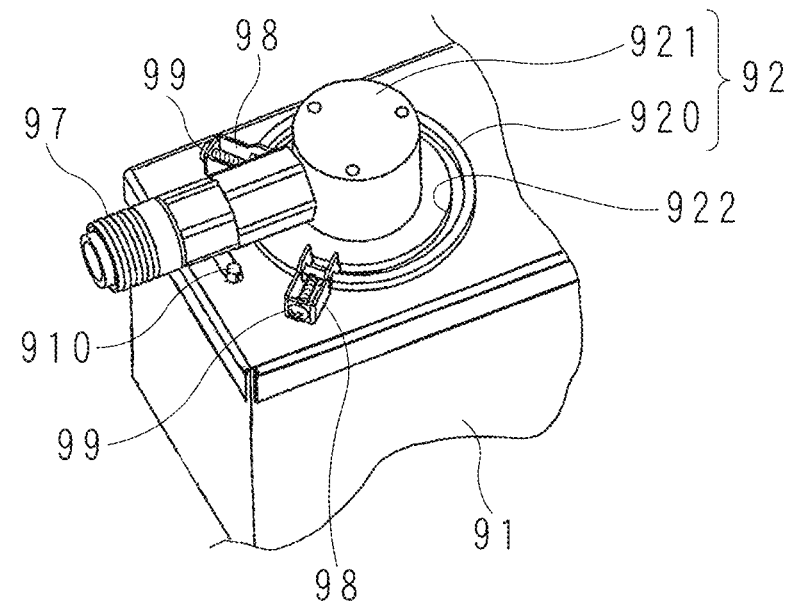

FIGS. 7A and 7B are upper perspective views of the rotating table 92, illustrating its structure. The rotating table 92 is a stepped disk member including: a large diameter portion 920 exposed at the upper surface of the driving box 91; and a small diameter portion 921 continuous with the top of the large diameter portion 920 such that the small diameter portion 921 is coaxial with the large diameter portion 920. The exit side connection 97 mentioned above is protruded radially outward from the peripheral surface of the small diameter portion 921. The upper surface of the small diameter portion 921 is provided with a plurality of screw holes for fixation of the supporting leg 93 described above.

The upper surface of the large diameter portion 920 is provided with a recessed groove 922 defined along the peripheral edge of the upper surface such that the recessed groove 922 forms a predetermined angle. Pressing pieces 98 are detachably attachable to the recessed groove 922 at suitable positions within the range in which the recessed groove 922 is formed. FIG. 7A illustrates the rotating table 92, with the pressing pieces 98 detached from the recessed groove 922. FIG. 7B illustrates the rotating table 92, with the two pressing pieces 98 attached to the recessed groove 922 at positions away from each other by a central angle of about 90 degrees therebetween. The pressing pieces 98 clamp the inner surface of the recessed groove 922 and the peripheral surface of the large diameter portion 920 by tightening fixation screws 99. The pressing pieces 98 are thus attached to the recessed groove 922 such that the pressing pieces 98 protrude outward from the outer periphery of the large diameter portion 920. The pressing pieces 98 are moved on the upper surface of the driving box 91 in accordance with rotation of the rotating table 92.

The upper surface of the driving box 91 is provided with a selector lever 910 protruded therefrom on a route for movement of the pressing pieces 98. The selector lever 910 abuts against one of the two pressing pieces 98, which move in accordance with rotation of the rotating table 92, and falls down so as to change the state of a selector switch (not illustrated) inside the driving box 91. The selector switch is a switch to change the rotation direction of a motor for driving the rotating table 92 to a forward direction or a reverse direction. The rotation direction of the rotating table 92 is reversed each time one of the two pressing pieces 98 abuts against the selector lever 910.

When the pressing pieces 98 are attached to the recessed groove 922 at the positions illustrated in FIG. 7B, the rotating table 92 changes its rotation direction at an angle of about 90 degrees so as to make repetitive rotations. The angular range of the repetitive rotations may be set suitably within the range in which the recessed groove 922 is formed by changing the positions of the pressing pieces 98 attached. When no pressing pieces 98 are attached to the recessed groove 922 as illustrated in FIG. 7A, the rotating table 92 rotates continuously in one direction.

Starting the automatic operation to be performed by the sterilizing apparatus structured as described above involves: bringing the spray gun 2, which is attached to the mounting stand 9, into the target space; placing the spray gun 2 on a floor surface while adjusting the height and elevation angle of the spray gun 2; operating the control panel 8 placed outside the target space; making settings necessary for the timer setter 82; and selecting the automatic operation using the operation selector switch 81. Thus, the solenoid selector valve 85 inside the control panel 8 is opened at a predetermined start time, so that the carbon dioxide gas within the gas cylinder 1 is supplied to the spray gun 2 through the output hose 100, the first coupling hose 101, and the second coupling hose 102. The spray gun 2 carries out the above-described medical fluid spraying for a predetermined period of time using, as a carrier gas, the carbon dioxide gas supplied. During this spraying, the trigger of the spray gun 2 is fixed at a position where the trigger is pulled.

The medical fluid is sprayed from the spray gun 2 while the set elevation angle is maintained and the orientation of the spray gun 2 is changed within a plane in accordance with rotation of the rotating table 92. Accordingly, the sterilizing apparatus is able to scatter the medical fluid effectively so as to sterilize the entire target space with reliability. A planar spraying range of the medical fluid within the target space is set by selecting a rotation mode (e.g., a repetitive rotation mode or a continuous rotation mode) for the rotating table 92 in accordance with the location of the spray gun 2 placed. When the target space is wide, more than one spray gun 2 attached to the mounting stand 9 may be prepared and suitably placed in a distributed manner, making the sterilizing apparatus adaptable to such a situation.

When the manual operation is selected by operating the operation selector switch 81 on the control panel 8, the solenoid selector valve 85 is opened, so that the above-described medical fluid scattering is carried out continuously, thus making it possible to sterilize the target space similarly to the automatic operation. The process of sterilizing the target space by the manual operation continues until the non-operation mode is selected by operating the operation selector switch 81.

The sterilizing apparatus according to Embodiment 2, which has been described thus far, makes it unnecessary to place an operator wearing protectors, such as a mask and goggles, within the target space. This makes it possible to save labor and reduce the burden on the operator.

The embodiments disclosed herein are to be considered as not limitative but illustrative in all respects. The scope of the present invention is defined not by the above description but by the claims and is intended to include all changes falling within the meaning and range equivalent to the claims. It is to be noted that, as used herein and in the appended claims, the singular forms "a", "an", and "the" include plural referents unless the context clearly dictates otherwise.

What is claimed is:

1. A sterilizing apparatus comprising:
    a medical fluid container storing a medical fluid containing alcohol;
    a gas cylinder filled with pressurized carbon dioxide gas;
    a spray gun connected with the medical fluid container and the gas cylinder, the sterilizing apparatus being configured to spray the medical fluid into a target space under action of the carbon dioxide gas injected from a nozzle tip of the spray gun;
    a control valve to increase and/or decrease an amount of the carbon dioxide gas to be injected, thus adjusting an amount of the medical fluid to be sprayed;
    a mounting stand having a rotating table to which the spray gun is attached;
    a motor drive disposed on the mounting stand that rotates the rotating table about a vertical axis extending above a floor surface in the target space so that the spray gun also rotates about the vertical axis; and
    a reverse selector that automatically reverses a direction of rotation of the rotating table between a predetermined angular range,
    wherein the reverse selector comprises a groove formed over a predetermined angle around the vertical axis on a top surface of the rotating table, a pressing piece that is detachably attached to the groove, and a selector lever arranged in a moving path of the pressing piece,
    wherein the pressing piece moves along the moving path in response to rotation of the rotating table, and
    wherein the selector lever is operably connected to the motor drive to switch the direction of rotation of the rotating table between a forward direction and a reverse direction when the pressing piece is caused to abut against the selector lever during rotation.

2. The sterilizing apparatus according to claim 1, further comprising:
    a gas hose extending from the gas cylinder and connected to the spray gun,
    wherein the control valve is interposed between the gas hose and the spray gun.

3. The sterilizing apparatus according to claim 1, wherein the medical fluid container is connected to the spray gun through a flexible medical fluid hose.

4. The sterilizing apparatus according to claim 1, wherein the spray gun is attached to the mounting stand such that the spray gun has a changeable elevation angle.

5. The sterilizing apparatus according to claim 1, further comprising:
    a timer setter; and
    a solenoid selector valve that opens and closes in accordance with a setting of the timer setter to allow selection between supply and interruption of the carbon dioxide gas to the spray gun.

* * * * *